United States Patent
Chen et al.

(10) Patent No.: US 9,550,886 B2
(45) Date of Patent: Jan. 24, 2017

(54) STABILIZER AND COMPOSITION INCLUDING THE SAME

(71) Applicant: DOUBLE BOND CHEMICAL IND., CO., LTD., New Taipei (TW)

(72) Inventors: Chiung-Ta Chen, New Taipei (TW); Chih-Wei Lin, New Taipei (TW); Ming-Yang Chien, New Taipei (TW); En-Ching Wang, New Taipei (TW); Chien-Liang Liu, Taipei (TW)

(73) Assignee: DOUBLE BOND CHEMICAL IND., CO., LTD., New Taipei (TW)

( * ) Notice: Subject to any disclaimer, the term of this patent is extended or adjusted under 35 U.S.C. 154(b) by 114 days.

(21) Appl. No.: 14/166,792

(22) Filed: Jan. 28, 2014

(65) Prior Publication Data
US 2015/0141557 A1 May 21, 2015

(30) Foreign Application Priority Data
Nov. 21, 2013 (TW) ................. 102142502 A

(51) Int. Cl.
| | |
|---|---|
| *C08K 5/52* | (2006.01) |
| *C07F 9/06* | (2006.01) |
| *C07F 9/59* | (2006.01) |
| *C08K 5/134* | (2006.01) |
| *C08K 5/3435* | (2006.01) |
| *C07F 9/145* | (2006.01) |

(52) U.S. Cl.
CPC ............ *C08K 5/52* (2013.01); *C07F 9/062* (2013.01); *C07F 9/145* (2013.01); *C07F 9/595* (2013.01); *C08K 5/134* (2013.01); *C08K 5/3435* (2013.01)

(58) Field of Classification Search
CPC ......... C08K 5/52; C08K 5/134; C08K 5/3435; C07F 9/062; C07F 9/595; C07F 9/145
See application file for complete search history.

(56) References Cited

U.S. PATENT DOCUMENTS

| | | | |
|---|---|---|---|
| 2006/0122076 A1* | 6/2006 | Malz .................. | C08K 5/13 508/478 |
| 2010/0240810 A1* | 9/2010 | King .................. | C07F 9/145 524/91 |
| 2015/0013755 A1* | 1/2015 | Ikenaga et al. ............ | 136/251 |

FOREIGN PATENT DOCUMENTS

| | | |
|---|---|---|
| EP | 1853660 | 6/2010 |
| TW | 200722508 | 6/2007 |

OTHER PUBLICATIONS

DBC Bonding Partnership, Additives for Plastics and Coatings, 2007, p. 1-4.*
"Office Action of Taiwan Counterpart Application", issued on Jun. 15, 2015, p. 1-p. 6.

* cited by examiner

*Primary Examiner* — Robert Jones, Jr.
(74) *Attorney, Agent, or Firm* — Jianq Chyun IP Office

(57) ABSTRACT

A stabilizer including a first component and a second component. The first component is a compound represented by the formula (1).

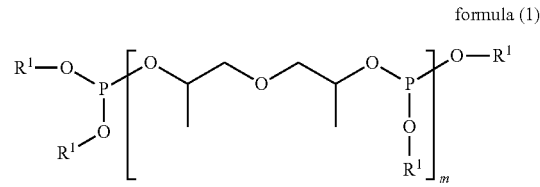

formula (1)

The second component is a compound represented by the formula (2).

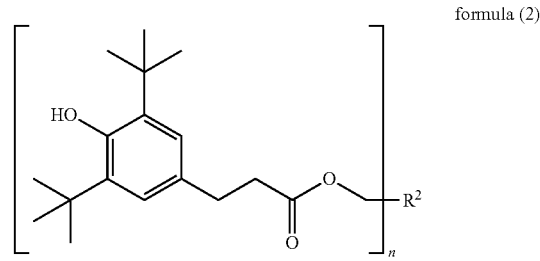

formula (2)

4 Claims, No Drawings

STABILIZER AND COMPOSITION INCLUDING THE SAME

CROSS-REFERENCE TO RELATED APPLICATION

This application claims the priority benefit of Taiwan application serial no. 102142502, filed on Nov. 21, 2013. The entirety of the above-mentioned patent application is hereby incorporated by reference herein and made a part of this specification.

BACKGROUND OF THE INVENTION

Field of the Invention

The invention relates to a stabilizer, and more particularly, to a stabilizer for a polymer.

Description of Related Art

With the development of the chemical industry, synthetic polymers have been widely applied in various fields such as adhesives, photoresists, electrolyte membrane of fuel cells, and insulating materials, etc.

In general, polymers need to subject to high temperature processing and are used under light and heat. Therefore, oxidation and changes in the chemical structure of the polymer during processing or use cause thermal degradation to the polymer. To improve the issue, various additives are usually added to the polymer to reduce the degree of thermal degradation. The additives are, for instance, antioxidants or stabilizers, etc.

US2011/0130492 discloses a composition including a polyether polyol, a polyester polyol, polyurethane, and a hindered amine light stabilizer. EP1853660 discloses a composition including polymers such as the polyether polyol, the polyester polyol, and polyurethane, bis(1,2,2,6,6-pentamethyl-4-piperidinyl)-((3,5-bis(1,1-dimethylethyl)-4-hydroxyphenyl)methyl)butylmalonate, and a calcium salt of (((1,1-dimethylethyl)-4-hydroxyphenyl)methyl)ethylphosphonate. WO2004/068217 discloses a composition in which bis(1,2,2,6,6-pentamethyl-4-piperidinyl)-((3,5-bis(1,1-dimethylethyl)-4-hydroxyphenyl)methyl)butylmalonate and pentaerythritol tetrakis(3-(3,5-di-tert-butyl-4-hydroxyphenyl)propionate) are in a light-colored polyurethane film or a light-colored polyester polyol.

Although currently many stabilizers have been developed for preventing thermal degradation of the polymer, issue of thermal degradation of the polymer still exist for the compositions or polymers using the stabilizers under the condition of heat.

As a result, the development of a stabilizer suitable for polymers is urgently needed for preventing issue of thermal degradation of the polymer and to increase the degree of thermal degradation resistance of the polymer.

SUMMARY OF THE INVENTION

The invention provides a stabilizer for a polymer, thereby preventing chemical changes to the polymer such as thermal degradation due to heating.

The invention provides a stabilizer. The stabilizer includes a first component and a second component. The first component is a compound represented by formula (1),

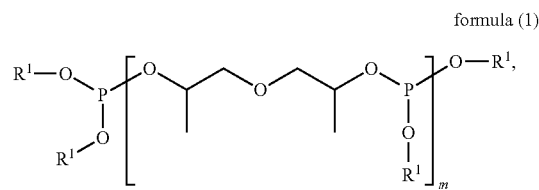

formula (1)

wherein $R^1$ is selected from the group consisting of a $C_1$-$C_{18}$ alkyl group, a $C_1$-$C_{18}$ alkyl group having a substituent, a $C_6$-$C_{15}$ aryl group, a $C_6$-$C_{15}$ aryl group having a substituent, a $C_6$-$C_{15}$ heterocyclic group, and a $C_6$-$C_{15}$ heterocyclic group having a substituent, and m is selected from integrals of 1 to 8.

The second component is a compound represented by formula (2),

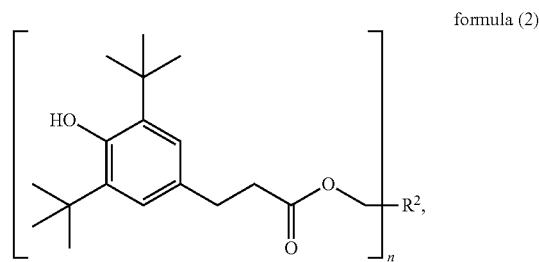

formula (2)

wherein n is 1 or 4, when n is 1, $R^2$ is a $C_1$-$C_{18}$ alkyl group, and when n is 4, $R^2$ is 2,2-dimethylprop-1,3,1',1''-tetrayl.

In an embodiment of the invention, the first component is selected from the group consisting of a compound represented by formula (1-1), a compound represented by formula (1-2), and a compound represented by formula (1-3),

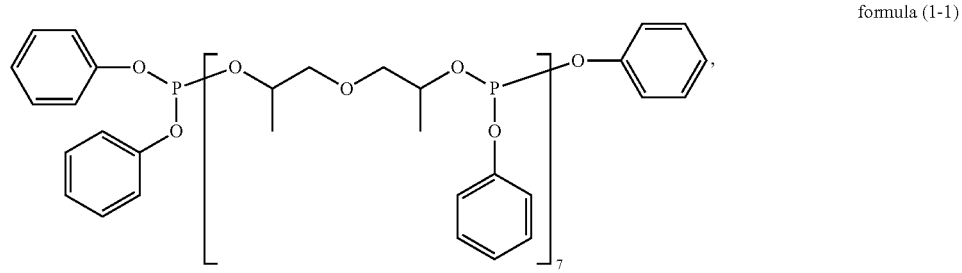

formula (1-1)

-continued formula (1-2)

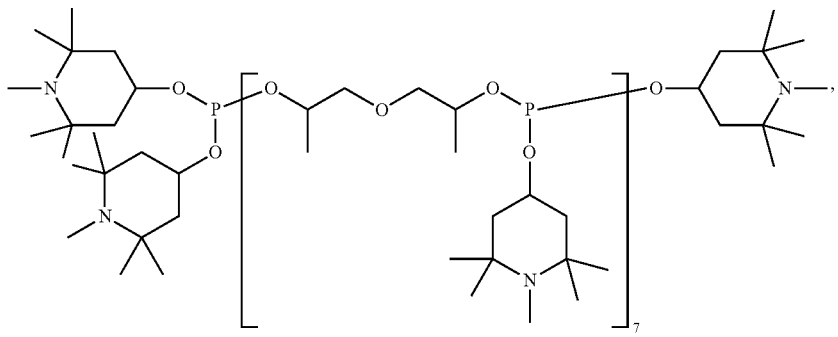

formula (1-3)

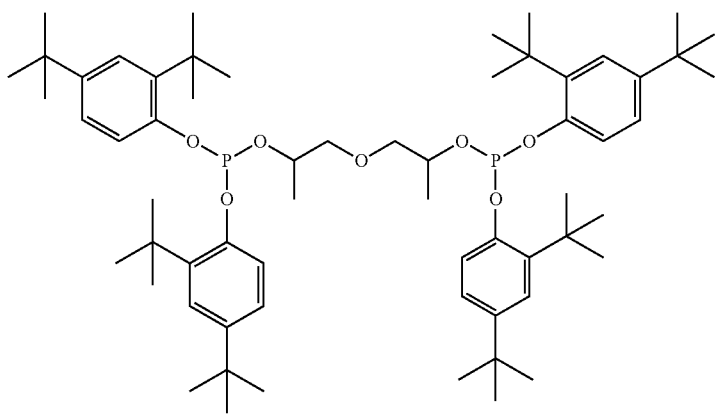

In an embodiment of the invention, based on 100 wt % of the first component and the second component, the content of the first component is 10 wt % to 60 wt % and the content of the second component is 40 wt % to 90 wt %.

In an embodiment of the invention, the second component is selected from the group consisting of methyl 3-(3,5-di-tert-butyl-4-hydroxyphenyl)propionate, heptyl 3-(3,5-di-tert-butyl-4-hydroxyphenyl)propionate, octyl 3-(3,5-di-tert-butyl-4-hydroxyphenyl)propionate, and nonyl 3-(3,5-di-tert-butyl-4-hydroxyphenyl)propionate.

In an embodiment of the invention, based on 100 wt % of the first component and the second component, the content of the first component is 10 wt % to 60 wt %, the content of heptyl 3-(3,5-di-tert-butyl-4-hydroxyphenyl)propionate, octyl 3-(3,5-di-tert-butyl-4-hydroxyphenyl)propionate, and nonyl 3-(3,5-di-tert-butyl-4-hydroxyphenyl)propionate of the second component is 20 wt % to 80 wt %, and the content of methyl 3-(3,5-di-tert-butyl-4-hydroxyphenyl)propionate of the second component is 10 wt % to 70 wt %.

The invention also provides a stabilizer. The stabilizer includes the first component.

The invention further provides a composition. The composition includes a polymer and the stabilizer, wherein based on a content of 100 parts by weight of the polymer, the content of the stabilizer is 0.01 parts by weight to 10 parts by weight.

In an embodiment of the invention, the polymer is selected from the group consisting of a polyester polyol, a polyether polyol, an acrylic polyol, a polycarbonate polyol, a polybutadiene polyol, a hydrogenated polybutadiene polyol, a functionalized polyether, and polyurethane.

According to the above, in the invention, by adding the stabilizer including the first component, the second component, or both of the two components to a polymer, known issue of thermal degradation of the polymer may be effectively improved.

To make the above features and advantages of the invention more comprehensible, several embodiments are described in detail as follows.

DESCRIPTION OF EMBODIMENTS

The invention provides a stabilizer for a polymer, including a first component, a second component, or a combination thereof. Also, the stabilizer for the polymer is preferably the first component or the combination of the first component and the second component. In the following, each components of the stabilizer of the invention are described in detail. Moreover, if needed, other additives may also be added to the polymer.

First Component

The first component is a poly(dipropylene glycol) phosphite-based compound. Specifically, the first component may be a compound represented by formula (1), formula (1)

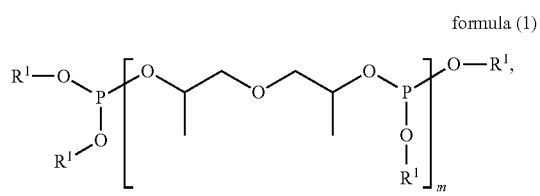

wherein $R^1$ is selected from the group consisting of a $C_1$-$C_{18}$ alkyl group, a $C_1$-$C_{18}$ alkyl group having a substituent, a $C_6$-$C_{15}$ aryl group, a $C_6$-$C_{15}$ aryl group having a substituent, a $C_6$-$C_{15}$ heterocyclic group, and a $C_6$-$C_{15}$ heterocyclic group having a substituent, and m is selected from integrals of 1 to 8.

When $R^1$ is the $C_1$-$C_{18}$ alkyl group, the alkyl group may be a straight chain or a branch chain alkyl group. Specifically, $R^1$ is methyl, ethyl, n-propyl, isopropyl, n-butyl, isobutyl, tert-butyl, tert-pentyl, n-pentyl, n-hexyl, n-heptyl, n-octyl, iso-octyl, 2-ethylhexyl, n-nonyl, iso-nonyl, n-decyl, undecyl, dodecyl, tridecyl, branched tridecyl, tetradecyl, pentadecyl, branched pentadecyl, hexadecyl, octadecyl (stearyl group), or the like. When $R^1$ is the $C_1$-$C_{18}$ alkyl group having a substituent, the substituent is a straight chain or a branch chain $C_1$-$C_{18}$ alkyl group or a $C_6$-$C_{15}$ aryl group, wherein the alkyl group is such as the alkyl group described above, and the aryl group is a homocyclic aryl group having one or a plurality of condensed rings. It should be noted that, the substituent may be 1 or more than 1.

When $R^1$ is the $C_6$-$C_{15}$ aryl group, the aryl group may be a homocyclic aryl group having one or a plurality of condensed rings. Specifically, $R^1$ is phenyl, naphthyl, phenanthryl, naphthacenyl, fluorenyl, pyrenyl, and the like. When $R^1$ is the $C_6$-$C_{15}$ aryl group having a substituent, the substituent is a straight chain or a branch chain $C_1$-$C_{18}$ alkyl group or a $C_6$-$C_{15}$ aryl group, wherein the alkyl group and the aryl group are such as the alkyl group and the aryl group described above. It should be noted that, the substituent may be 1 or more than 1.

When $R^1$ is a $C_6$-$C_{15}$ heterocyclic group, the heterocyclic group is a group in which one carbon of an aryl group or a cycloalkyl group is substituted by a heteroatom. Examples of the heteroatom include a nitrogen atom, an oxygen atom, and a sulfur atom. Specifically, the heterocyclic group is, for instance, an imidazolyl group, a pyridyl group, a quinolyl group, a furyl group, a thienyl group, a piperidinyl group, a morpholinyl group, a benzoxazolyl group, a benzimidazolyl group, a benzothiazolyl group, a carbazolyl group, an azepinyl group, and the like. When $R^1$ is a $C_6$-$C_{15}$ heterocyclic group having a substituent, the substituent is a group substituting a hydrogen of the heterocyclic group (such as a hydrogen on carbon or nitrogen). Furthermore, the substituent is a straight chain or a branch chain $C_1$-$C_{18}$ alkyl group or a $C_6$-$C_{15}$ aryl group, wherein the alkyl group and the aryl group are such as the alkyl group and the aryl group described above. It should be noted that, the substituent may be 1 or more than 1.

Examples of the first component include the compound represented by formula (1-1), the compound represented by formula (1-2), the compound represented by formula (1-3), or the like, or a combination thereof.

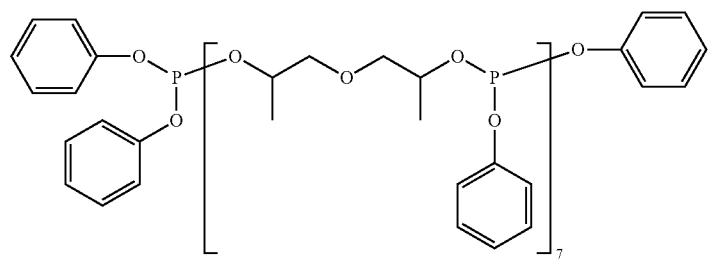

formula (1-1)

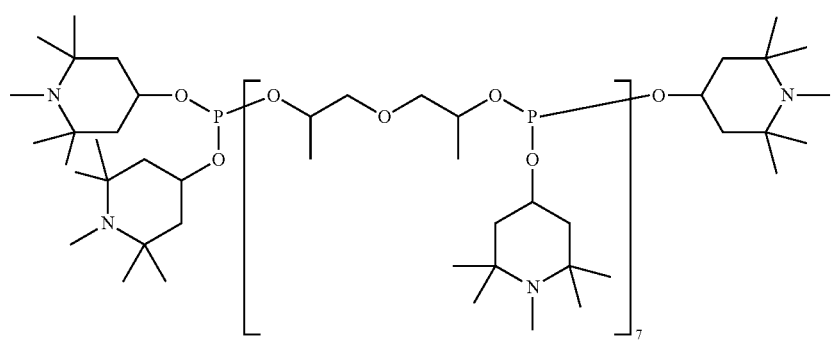

formula (1-2)

-continued

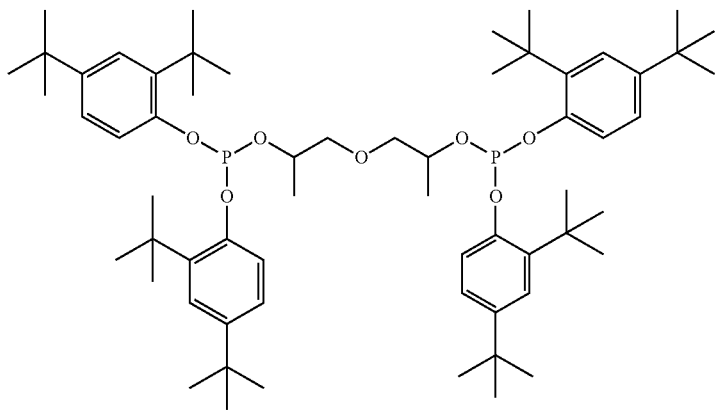

The compound represented by formula (1-1) is a poly(dipropylene glycol) phenyl phosphite. Specifically, an example of commercial products of the compound represented by formula (1-1) is oxybispropylenebis(1,5,9,13,17,21-hexamethyl-7,15,23,23-tetraphenoxy-3,6,8,11,14,16,19,22-octaoxa-7,15,23-triphosphatricos-1-yl)(phenyl)phosphine (product name: Chinox TP-20, CAS No. 80584-86-7, manufactured by DOUBLE BOND CHEMICAL IND., CO., LTD.).

An example of commercial products of the compound represented by formula (1-2) is 4-((8-((bis(((1,2,2,6,6-pentamethylpiperidin-4-yl)phosphanyl)oxy)-4-methyl-1-(1,2,2,6,6-pentamethylpiperidin-4-yl)-1,3,6-trioxa-2-phosphanonan-2-yl)oxy)-1,2,2,6,6-pentamethylpiperidine (product name: Chinox MP, manufactured by DOUBLE BOND CHEMICAL IND., CO., LTD.).

An example of commercial products of the compound represented by formula (1-3) is 1-(2-bis(2,4-di-tert-butylphenoxy)phosphanyloxypropoxy)propan-2-yl-bis(2,4-di-tert-butylphenyl)phosphate (product name: Chinox TP-80, CAS No. 1204606-71-2, manufactured by DOUBLE BOND CHEMICAL IND., CO., LTD.)

It should be noted that, the first component is preferably from a group consisting of the compound represented by formula (1-1) and the compound represented by formula (1-2), and more preferably is the compound represented by formula (1-2).

By adding the first component to the stabilizer, the stabilizer may be made to prevent the polymer from chemical changes such as thermal degradation due to heat much better.

Based on 100 wt % of the first component and the second component, the content of the first component may be 10 wt % to 60 wt %, preferably 15 wt % to 50 wt %, and more preferably 20 wt % to 40 wt %. When the content of the first component is less than 10 wt % or more than 60 wt %, an effect of the stabilizer to prevent the polymer from thermal degradation due to heat is poor.

Second Component

The second component is alkyl 3-(3,5-di-tert-butyl-4-hydroxyphenyl)propionate. Specifically, the second component may be a compound represented by formula (2),

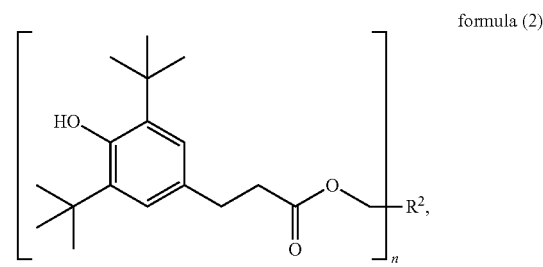

wherein n is 1 or 4, when n is 1, $R^2$ is a $C_1$-$C_{18}$ alkyl group, and when n is 4, $R^2$ is 2,2-dimethylprop-1,3,1',1"-tetrayl.

When $R^2$ is the $C_1$-$C_{18}$ alkyl group, the alkyl group may be a straight chain or a branch chain alkyl group. Specifically, $R^2$ is methyl, ethyl, n-propyl, isopropyl, n-butyl, isobutyl, tert-butyl, tert-pentyl, n-pentyl, n-hexyl, n-heptyl, n-octyl, iso-octyl, 2-ethylhexyl, n-nonyl, iso-nonyl, n-decyl, undecyl, dodecyl, tridecyl, branched tridecyl, tetradecyl, pentadecyl, branched pentadecyl, hexadecyl, octadecyl (stearyl group), or the like. It should be noted that, in formula (2), $R^2$ is preferably selected from the group consisting of $C_1$, $C_7$, $C_8$, and $C_9$ alkyl group.

Examples of the second component include methyl 3-(3,5-di-tert-butyl-4-hydroxyphenyl)propionate, ethyl 3-(3,5-di-tert-butyl-4-hydroxyphenyl)propionate, propyl 3-(3,5-di-tert-butyl-4-hydroxyphenyl)propionate, butyl 3-(3,5-di-tert-butyl-4-hydroxyphenyl)propionate, pentyl 3-(3,5-di-tert-butyl-4-hydroxyphenyl)propionate, hexyl 3-(3,5-di-tert-butyl-4-hydroxyphenyl)propionate, heptyl 3-(3,5-di-tert-butyl-4-hydroxyphenyl)propionate, octyl 3-(3,5-di-tert-butyl-4-hydroxyphenyl)propionate, nonyl 3-(3,5-di-tert-butyl-4-hydroxyphenyl)propionate, decyl 3-(3,5-di-tert-butyl-4-hydroxyphenyl)propionate, undecyl 3-(3,5-di-tert-butyl-4-hydroxyphenyl)propionate, dodecyl 3-(3,5-di-tert-butyl-4-hydroxyphenyl)propionate, octadecyl 3-(3,5-di-tert-butyl-4-hydroxyphenyl)propionate, or the like, or a combination thereof.

The second component is preferably selected from the group consisting of methyl 3-(3,5-di-tert-butyl-4-hydroxyphenyl)propionate, heptyl 3-(3,5-di-tert-butyl-4-hydroxyphenyl)propionate, octyl 3-(3,5-di-tert-butyl-4-hydroxyphenyl)propionate, and nonyl 3-(3,5-di-tert-butyl-4-hydroxyphenyl)propionate.

By adding the second component to the stabilizer, the stabilizer may be made to prevent the polymer from chemical changes such as thermal degradation due to heat much better, and preparation costs of the stabilizer can further be reduced. It should be noted that, based on 100 wt % of the first component and the second component, the content of the second component may be 40 wt % to 90 wt %, preferably 50 wt % to 80 wt %, and more preferably 60 wt % to 70 wt %. When the content of the second component is less than 40 wt % or more than 90 wt %, the effect of the stabilizer to prevent the polymer from thermal degradation due to heat is poor.

In the preferred embodiment of the invention, when the second component is consisted of methyl 3-(3,5-di-tert-butyl-4-hydroxyphenyl)propionate, heptyl 3-(3,5-di-tert-butyl-4-hydroxyphenyl)propionate, octyl 3-(3,5-di-tert-butyl-4-hydroxyphenyl)propionate, and nonyl 3-(3,5-di-tert-butyl-4-hydroxyphenyl)propionate, the content of the first component is wt % to 60 wt %, the content of heptyl 3-(3,5-di-tert-butyl-4-hydroxyphenyl)propionate, octyl 3-(3,5-di-tert-butyl-4-hydroxyphenyl)propionate, and nonyl 3-(3,5-di-tert-butyl-4-hydroxyphenyl)propionate of the second component is 20 wt % to 80 wt %, and the content of methyl 3-(3,5-di-tert-butyl-4-hydroxyphenyl)propionate of the second component is 10 wt % to wt %.

Additive

The stabilizer of the invention may optionally further include an additive. Specifically, the additive includes an antioxidant, a UV absorber and a light stabilizer, a metal deactivator, phosphite and phosphonite, hydroxylamines, a thiosynergist, a peroxide scavenger, a polyamide stabilizer, a basic costabilizer, a nucleating agent, a filler, a reinforcing agent, other additives, benzofuranones and indolinones, a flame retardant.

Examples of the antioxidant include alkylated monophenols, alkylthiomethylphenols, hydroquinones and alkylated hydroquinones, tocopherols, hydroxylated thiodiphenyl ethers, alkylidenebisphenols, O-, N-, and S-benzyl compounds, hydroxybenzylated malonates, aromatic hydroxybenzyl compounds, triazine compounds, benzylphosphonates, acylaminophenols, esters of β-(3,5-di-tert-butyl-4-hydroxyphenyl) propionic acid with a mono- or polyol, esters of β-(5-tert-butyl-4-hydroxy-3-methylphenyl)propionic acid with a mono- or polyol, esters of β-(3,5-dicyclohexyl-4-hydroxyphenyl)propionic acid with a mono- or polyol, esters of 3,5-di-tert-butyl-4-hydroxyphenyl acetic acid with a mono- or polyol, amides of β-(3,5-di-tert-butyl-4-hydroxyphenyl)propionic acid, ascorbic acid, or amine-based antioxidants.

Examples of alkylated monophenols include 2,6-di-tert-butyl-4methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutylphenol, 2,6-di-tert-butyl-4-sec-butylphenol, 2,6-di-tert-butyl-4-nonylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenol in which a side chain thereof is a straight chain or a branch chain, such as 2,6-di-nonyl-4-methylphenol, 2,4-dimethyl-6-(1'-methylundec-1'-yl)phenol, 2,4-dimethyl-6-(1'-methylheptadec-1'-yl) phenol and 2,4-dimethyl-6-(1'-methyltridec-1'-yl)phenol, or the like, or a combination thereof.

Examples of alkylthiomethylphenols include 2,4-dioctylthiomethyl-6-tert-butylphenol, 2,4-dioctylthiomethyl-6-methylphenol, 2,4-dioctylthiomethyl-6-ethylphenol, 2,6-didodecylthiomethyl-4-nonylphenol, or the like, or a combination thereof.

Examples of hydroquinones and alkylated hydroquinones include 2,6-di-tert-butyl-4-methoxyphenol, 2,5-di-tert-butylhydroquinone, 2,5-di-t-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate, or a combination of the compounds.

Examples of tocopherols include α-tocopherol, β-tocopherol, γ-tocopherol, δ-tocopherol, and a mixture thereof (vitamin E), or the like, or a combination thereof.

Examples of hydroxylated thiodiphenyl ethers include 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl) disulfide, or the like, or a combination thereof.

Examples of alkylidenebisphenols include 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl]-terephthalate, 1,1-bis-(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra-(5-tert-butyl-4-hydroxy-2-methylphenyl)pentane, or the like, or a combination thereof.

Examples of the O-, N- and S-benzyl compounds include 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis (3,5-di-tert-butyl-4-hydroxybenzyl)sulfide, isooctyl-3,5-di-tert-butyl-4-hydroxybenzyl-mercapto acetate, or the like, or a combination thereof.

Examples of hydroxybenzylated malonates include di-octadecyl-2,2-bis(3,5-di-tert-butyl-2-hydroxybenzyl)malonate, di-octadecyl-2-(3-tert-butyl-4-hydroxy-5-methylbenzyl)malonate, di-dodecylmercaptoethyl-2,2-bis(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)-malonate, or the like, or a combination thereof.

Examples of the aromatic hydroxybenzyl compounds include 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol, or the like, or a combination thereof.

Examples of the triazine compounds include 2,4-bis(octylmercapto)-6-(3,5-di-tert-butyl-4-hydroxyanilino)-1,3,5- triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxy-phenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl)-4-hydroxybenzylisocyanurate, or the like, or a combination thereof.

Examples of benzylphosphonates include dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, or the like, or a combination thereof.

Examples of acylaminophenols include 4-hydroxylauranilide, 4-hydroxystearanilide, octyl N-(3,5-di-tert-butyl-4-hydroxyphenyl)carbamate, or the like, or a combination thereof.

Esters of β-(3,5-di-tert-butyl-4-hydroxyphenyl) propionic acid with a mono- or polyol, wherein the mono- or polyol are such as methanol, ethanol, n-octanol, i-octanol, octa-decanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane; alkyl esters of which a carbon number of β-(3,5-di-tert-butyl-4-hydroxyphenyl) propionic acid is 13 to 15 (CAS No. 171090-93-0), or the like, or a combination thereof.

Esters of β-(5-tert-butyl-4-hydroxy-3-methylphenyl)propionic acid with a mono- or polyol, wherein the mono- or polyol are such as methanol, ethanol, n-octanol, i-octanol, octa-decanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]undecane, or the like, or a combination thereof.

Esters of β-(3,5-dicyclohexyl-4-hydroxyphenyl)propionic acid with a mono- or polyol, wherein the mono- or polyol are such as methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane, or the like, or a combination thereof.

Esters of 3,5-di-tert-butyl-4-hydroxyphenyl acetic acid with a mono- or polyol, wherein the mono- or polyol are such as methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]-octane, or the like, or a combination thereof.

Examples of the amides of β-(3,5-di-tert-butyl-4-hydroxyphenyl)propionic acid include N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxypheny)propionyl)hydrazide, N,N'-bis[2-(3-[3,5-di-tert-butyl-4-hydroxyphenyl]-propionyloxy)ethyl]oxamide (Naugard XL-1, provided by Uniroyal), or the like, or a combination thereof.

Ascorbic Acid (Vitamin C)

Examples of the amine-based antioxidants include N,N'-di-isopropyl-p-phenylenediamine, N,N'-di-sec-butyl-p-phenylenediamine, N,N'-bis(1,4-dimethylphenyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methyl-heptyl)-N'-phenyl-p-phenylenediamine, N-cyclohexyl-N'-phenyl-p-phenylenediamine, 4-(p-toluenesulfamoyl)diphenyl amine, N,N'-dimethyl-N,N'-di-sec-butyl-p-phenylenediamine, diphenylamine, N-allyldiphenyl amine, 4-isopropoxydiphenyl amine, N-phenyl-1-naphthylamine, N-(4-tert-octylphenyl)-1-naphthylamine, N-phenyl-2-naphthylamine, 4,4'-bis(α,α-dimethylbenzyl)diphenylamine, a reaction product of N-phenylaniline, isobutylene, and 2,4,4-trimethylpentene, octylated diphenylamine (such as p,p'-di-tert-octyldiphenylamine), 4-n-butyl-aminophenol, 4-butyryl aminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-butylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octyl-phenothiazines, N-allylphenothiazine, N,N,N',N'-tetraphenyl-1,4-diaminobut-2-ene, or the like, or a combination thereof.

The UV absorber and the light stabilizer include 2-(2'-hydroxyphenyl)benzotriazoles, 2-hydroxybenzophenones, esters of substituted and unsubstituted benzoic acid, acrylates, nickel compounds, sterically hindered amines, oxamides, 2-(2-hydroxyphenyl)-1,3,5-triazines, or a combination thereof.

Examples of 2-(T-hydroxyphenyl)benzotriazoles include 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octyloxyphenyl)benzotriazole, 2-(3', 5'-di-tert-amyl-T-hydroxyphenyl)benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl) phenyl)-5-chlorobenzotriazole, 2-(3'-tert-butyl-5'-[2-(2-ethylhexyloxyl)carbonylethyl]-2'-hydroxyphenyl)-5-chlorobenzotiiazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl) phenyl)benzotriazole, 2-(3'-tert-butyl-T-hydroxy-5'-(2-octyloxycarbonylethyl)phenyl)benzotriazole, 2-(3'-tert-butyl-5'-[2-(2-ethylhexyloxyl)carbonylethyl]-2'-hydroxyphenyl) benzotriazole, 2-(3'-dodecyl-2'-hydroxy-5'-methylphenyl) benzotriazole, 2-(3'-tert-butyl-T-hydroxy-5'-(2-isooctyloxycarbonylethyl)phenylbenzotriazole, 2,2'-methylene-bis[4-(1,1,3,3-tetramethylbutyl)-6-benzotriazole-2-phenol]; the transesterification product of 2-[3'-tert-butyl-5'-(2-methoxycarbonylethyl)-2'-hydroxyphenyl]-2H-benzotriazole with polyethylene glycol 300,

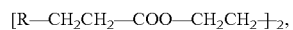

wherein R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)-phenyl]benzotriazole; 2-[2'-hydroxy-3'-(1,1,3,3-tetramethylbutyl)-5'-(α,α-dimethylbenzyl)-phenyl] benzotriazole, or a combination thereof.

Examples of 2-hydroxybenzophenones include 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives, or the like, or a combination thereof.

Examples of the esters of substituted and unsubstituted benzoic acid include 4-tert-butyl-phenylsalicylate, phenyl salicylate, octylphenyl salicylate, dibenzoyl resorcinol, bis (4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate, or a combination thereof.

Examples of acrylates include ethyl α-cyano-β,β-diphenylacrylate, isooctyl α-cyano-β,β-diphenylacrylate, methyl α-carbomethoxycinnamate, methyl α-cyano-β-methyl-β-methoxycinnamate, butyl α-cyano-β-methyl-p-methoxycinnamate, methyl α-carbomethoxy-p-methoxycinnamate, N-(β-carbomethoxy-β-cyanovinyl)-2-methylindoline, neopentyl tetra(α-cyano-β,β-diphenylacrylate), or the like, or a combination thereof.

Examples of the nickel compounds include nickel complexes of 2,2'-thio-bis[4-(1,1,3,3-tetramethylbutyl)phenol] with or without other ligands (such as n-butylamine, triethanolamine, or N-cyclohexyldiethanolamine), such as the 1:1 or 1:2 complex, nickel dibutyldithiocarbamate, nickel salts of a monoalkyl ester (such as methyl or ethyl ester) of 4-hydroxy-3,5-di-tert-butylbenzylphosphonic acid, nickel complexes of ketoxime (such as 2-hydroxy-4-methylphenylundecylketoxime), nickel complexes of 1-phenyl-4-lauroyl-5-hydroxypyrazole with or without other ligands, or the like, or a combination thereof.

Examples of sterically hindered amines include bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, a condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)triacetate, tetrakis(2,2,6,6-tetramethyl-4-piperidyl)-1,2,3,4-butanetetracarboxylate, 1,1'-(1,2-ethanediyl)-bis(3,3,5,5-tetramethyl-4-hexahydropiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl) malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-penta-methyl-4-piperidyl) pyrrolidine-2,5-dione, a mixture of 4-hexadecyloxy-2,2,6,6-tetramethylpiperidine and 4-stearyloxy-2,2,6,6-tetramethylpiperidine, a condensate of N,N'-bis(2,2,6,6-tetramethyl-4-piperidyl)-hexamethylenediamine and 4-cyclohexylamino-2,6-dichloro-1,3,5-triazine, a condensate of 1,2-bis(3-aminopropylamino)ethane, 2,4,6-trichloro-1,3,5-triazine, and 4-butylamino-2,2,6,6-tetramethylpiperidine (CAS Reg. No. [136504-96-6]), a condensate of 1,6-hexanediamine and 2,4,6-trichloro-1,3,5-triazine and N,N-dibutylamine and 4-butylamino-2,2,6,6-tetramethylpiperidine (CAS Reg. No. [192268-64-7]), N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxo-spiro [4,5]decane, a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)ethene, N,N'-bis-formyl-N,N-bis(2,2,6,6-tetramethyl-4-piperidyl)hexamethylenediamine, a diester of 4-methoxymethylene malonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine, 2,4-bis[N-(1-cyclohexyloxy-2,2,6,6-tetramethylpiperidine-4-yl)-N-butylamino]-6-(2-hydroxyethyl)amino-1,3,5-triazine, 1-(2-hydroxy-2-methylpropoxy)-4-octadecanoyloxy-2,2,6,6-tetramethylpiperidine, 5-(2-ethylhexanoyl)oxymethyl-3,3,5-trimethyl-2-morpholinone, Sanduvor (Clariant Corp.); CAS Reg. No. 106917-31-1, 5-(2-ethylhexanoyl)oxymethyl-3,3,5-trimethyl-2-morpholinone, the reaction product of 2,4-bis [(1-cyclohexyloxy-2,2,6,6-piperidine-4-yl)butylamino]-6-chloro-S-triazine with N,N'-bis(3-aminopropyl) ethylenediamine), 1,3,5-tris(N-cyclohexyl-N-(2,2,6,6-tetramethylpiperazine-3-one-4-yl)amino)-s-triazine, 1,3,5-tris(N-cyclohexyl-N-(1,2,2,6,6-pentamethylpiperazine-3-one-4-yl)amino)-s-triazine, or the like, or a combination thereof.

Examples of oxamides include 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, a mixture of 2-ethoxy-5-tert-butyl-2'-ethoxanilide and 2-ethoxy-2'-ethyl-5,4'-di-tert-butoxanilide, a mixture of o-methoxy-disubstituted oxanilide and p-methoxy-disubstituted oxanilide and a mixture of o-ethoxydisubstituted oxanilide and p-ethoxy-disubstituted oxanilide, or the like, or a combination thereof.

Examples of 2-(2-hydroxyphenyl)-1,3,5-triazines include 2,4,6-tris(2-hydroxy-4-octyloxyphenyl)-1,3,5-triazine, 2-(2-hydroxy-4-octyloxyphenyl)-4,6-bis(2,4-dimethyl-phenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxy)phenyl-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine, 2,4-bis(4-[2-ethylhexyloxy]-2-hydroxyphenyl)-6-(4-methoxyphenyl)-1,3,5-triazine, or the like, or a combination thereof.

Examples of the metal deactivators include N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)-thiopropionyldihydrazide, or the like, or a combination thereof.

Examples of thiosynergists include dimyristyl thiodipropionate, ditridecyl thiodipropionate, distearyl disulfide, or a similar compound thereof, or a combination of the compounds.

The phosphites and phosphonites are compounds represented by formula (3),

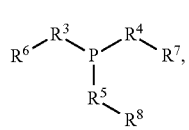

formula (3)

wherein $R^3$, $R^4$, and $R^5$ are each independently a single bond or oxygen, and $R^6$, $R^7$, and $R^8$ are each independently selected from the group consisting of a $C_1$-$C_{18}$ alkyl group, a $C_1$-$C_{18}$ alkyl group having a substituent, a $C_6$-$C_{15}$ aryl group, and a $C_6$-$C_{15}$ aryl group having a substituent.

$R^3$, $R^4$, and $R^5$ can each independently be the same or different groups, for instance, $R^3$ is the same as $R^4$ but is different from $R^5$, $R^3$ is the same as $R^5$ but is different from $R^2$, $R^4$ is the same as $R^5$ but is different from $R^3$, or all three are the same. It should be noted that, $R^3$, $R^4$, and $R^5$ are preferably the same groups and $R^3$, $R^4$, and $R^5$ are more preferably oxygen.

When $R^6$, $R^7$, and $R^8$ are each independently selected from a $C_1$-$C_{18}$ alkyl group, the alkyl group may be a straight chain or a branch chain alkyl group. Specifically, $R^6$, $R^7$, and $R^8$ are each independently methyl, ethyl, n-propyl, isopropyl, n-butyl, isobutyl, tert-butyl, tert-pentyl, n-pentyl, n-hexyl, n-heptyl, n-octyl, iso-octyl, 2-ethylhexyl, n-nonyl, iso-nonyl, n-decyl, undecyl, dodecyl, tridecyl, branched tridecyl, tetradecyl, pentadecyl, branched pentadecyl, hexadecyl, octadecyl (stearyl group), or the like. When $R^6$, $R^7$, and $R^8$ are each independently a $C_1$-$C_{18}$ alkyl group having a substituent, the substituent is a straight chain or a branch chain $C_1$-$C_{18}$ alkyl group or a $C_6$-$C_{15}$ aryl group, wherein the alkyl group and the aryl group are, for instance, the alkyl group and the aryl group described above. It should be noted that the substituent may be 1 or more than 1.

When $R^6$, $R^7$, and $R^8$ are each independently a $C_6$-$C_{15}$ aryl group, the aryl group may be a homocyclic aryl group having one or a plurality of condensed rings. Specifically, $R^6$, $R^7$, and $R^8$ are each independently a phenyl group, a naphthyl group, a phenanthryl group, a naphthacenyl group, a fluorenyl group, a pyrenyl group, or the like. When $R^6$, $R^7$, and $R^8$ are each independently a $C_6$-$C_{15}$ aryl group having a substituent, the substituent is a straight chain or a branch chain $C_1$-$C_{18}$ alkyl group or a $C_6$-$C_{15}$ aryl group, wherein the alkyl group and the aryl group are, for instance, the alkyl group or the aryl group described above. It should be noted that the substituent may be 1 or more than 1.

$R^6$, $R^7$, and $R^8$ can each independently be the same or different groups, for instance, $R^6$ is the same as $R^7$ but is different from $R^8$, $R^6$ is the same as $R^8$ but is different from $R^7$, $R^7$ is the same as $R^8$ but is different from $R^6$, all three are different, or all three are the same. Moreover, $R^6$, $R^7$, and $R^8$ can also be bonded to one another to form a cyclic structure. It should be noted that, $R^6$, $R^7$, and $R^8$ are preferably the same groups. Moreover, when $R^3$, $R^4$, and $R^5$ are oxygen and $R^6$, $R^7$, and $R^8$ are $C_1$-$C_{18}$ alkyl groups, $R^6$, $R^7$, and $R^8$ are preferably decyl, undecyl, dodecyl, hexadecyl, heptadecyl, or octadecyl groups. When $R^3$, $R^4$, and $R^5$ are oxygen and $R^6$, $R^7$, and $R^8$ are $C_6$-$C_{15}$ aryl groups having a substituent, $R^6$, $R^7$, and $R^8$ are preferably phenyl groups, wherein the substituent of the phenyl groups is a nonyl group or a tert-butyl group.

Specific example of the phosphites and phosphonites include triphenyl phosphite, diphenylalkyl phosphite, phenyldialkyl phosphite, tris(nonylphenyl) phosphite, tridecyl phosphite, triundecyl phosphite, tridodecyl phosphite, trioctadecyl phosphite, distearylpentaerythritol diphosphite, tris (2,4-di-tert-butylphenyl) phosphite, diisodecyl pentaerythritol diphosphite, bis(2,4-di-tert-butylphenyl)pentaerythritol diphosphite, bis(2,4-di-cumylphenyl)pentaerythritol diphosphite, bis(2,6-di-tert-butyl-4-methylphenyl)pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl)4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methyl-phenyl) methyl phosphite, bis(2,4-di-tert-butyl-6-methylphenyl) ethyl phosphite, 6-fluoro-2,4,8,10-tetra-tert-butyl-12-methyl-dibenz[d,g]-1,3,2-dioxaphosphocin, 2,2',2"-nitrilo[triethyltris(3,3',5,5'-tetra-tert-butyl-1,1'-biphenyl-2,2'-diyl) phosphite], 2-ethylhexyl(3,3',5,5'-tetra-tert-butyl-1,1'-biphenyl-2,2'-diyl)phosphite, 5-butyl-5-ethyl-2-(2,4,6-tri-tert-butyl-phenoxy)-1,3,2-dioxaphosphirane, or the like, or a combination thereof.

Examples of the hydroxylamine include N,N-dibenzylhydroxylamine, N,N-diethylhydroxylamine, N,N-dioctylhydroxylamine, N,N-dilaurylhydroxylamine, N,N-di-tetradecylhydroxylamine, N,N-di-hexadecylhydroxylamine, N,N-di-octadecylhydroxylamine, N-hexadecyl-N-octadecylhydroxyl amine, N-heptadecyl-N-octadecylhydroxylamine, N,N-dialkylhydroxylamine derived from hydrogenated tallow amine or the like, or a combination thereof.

Examples of the nitrones include N-benzyl-α-phenylnitrone, N-ethyl-α-methylnitrone, N-octyl-α-heptylnitrone, N-lauryl-α-undecylnitrone, N-tetradecyl-α-tridecylnitrone, N-hexadecyl-α-pentadecylnitrone, N-octadecyl-α-heptadecylnitrone, N-hexadecyl-α-heptadecylnitrone, N-octadecyl-α-pentadecylnitrone, N-heptadecyl-α-heptadecylnitrone, N-octadecyl-α-hexadecylnitrone, nitrone derived from N,N-dialkylhydroxylamine derived from hydrogenated tallow amine or the like, or a combination thereof.

Examples of thiosynergists include dilauryl thiodipropionate, dimistryl thiodipropionate, distearyl thiodipropionate or distearyl disulfide or the like, or a combination thereof.

Examples of the peroxide scavengers include esters of β-thiodipropionic acid (such as lauryl, stearyl, myristyl, or tridecyl esters), mercaptobenzimidazole or the zinc salt of 2-mercaptobenzimidazole, zinc dibutyldithiocarbamate, dioctadecyl disulfide, pentaerythritol tetrakis (β-dodecylmercapto)propionate, or the like, or a combination thereof.

Examples of the polyamide stabilizers include copper salts in combination with iodides and/or phosphorus compounds, salts of divalent manganese, or the like, or a combination thereof.

Examples of the basic costabilizers include melamine, polyvinylpyrrolidone, dicyandiamide, triallyl cyanurate, urea derivatives, hydrazine derivatives, amines, polyamides, polyurethanes, alkali metal saist and alkaline earth metal salts of higher fatty acids (such as calcium stearate, zinc stearate, magnesium behenate, magnesium stearate, sodium ricinoleate, potassium palmitate, antimony pyrocatecholate, or zinc pyrocatecholate), or the like, or a combination thereof.

Examples of the nucleating agents include inorganic substances such as talcum, metal oxides (such as titanium dioxide or magnesium oxide), and preferably are phosphate, carbonate, or sulfate of an alkaline earth metal; organic compounds such as monocarboxylic acids or polycarboxylic acids and salts thereof such as 4-tert-butylbenzoic acid, adipic acid, diphylacetic acid, sodium succinate or sodium benzoate; polymeric compounds, such as ionic copolymers (ionomers). Especially preferred are 1,3:2,4-bis(3',4'-dimethylbenzylidene)sorbitol, 1,3:2,4-di(paramethyldibenzylidene)sorbitol, and 1,3:2,4-di(benzylidene)sorbitol, or the like, or a combination thereof.

Examples of the fillers and the reinforcing agents include calcium carbonates, silicates, glass fibres, glass beads, asbestos, talc, kaolin, mica, barium sulfate, metal oxides and hydroxides, carbon black, graphite, wood flour and flours or fibres of other natural products, synthetic fibre or a similar compound thereof, or a combination of the compounds.

Examples of other additives include plasticisers, lubricants, emulsifiers, pigments, rheology additives, catalysts, flow-control agents, optical brighteners, antistatic agents, and blowing agents.

Examples of the benzofuranones and indolinones include those disclosed in U.S. Pat. No. 4,325,863, U.S. Pat. No. 4,338,244, U.S. Pat. No. 5,175,312, U.S. Pat. No. 5,216,052, U.S. Pat. No. 5,252,643, DE-A-4316611, DE-A-4316622, DE-A-4316876, EP-A-0589839, EP-A-0591102, EP-A-1291384, or 3-[4-(2-acetoxyethoxy)phenyl]-5,7-di-tert-butylbenzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethylphenyl)-5,7-di-tert-butylbenzofuran-2-one, 3-(2,3-dimethylphenyl)-5,7-di-tert-butylbenzofuran-2-one, 3-(2-acetyl-5-isooctylphenyl)-5-isooctylbenzofuran-2-one, or a combination of the compounds, or the like, or a combination thereof.

Examples of the flame retardants include halogenated benzenes, biphenyls, phenols, ethers or esters thereof, bisphenols, diphenyloxides, aromatic carboxylic acids or polyacids, anhydrides, amides or imides thereof; organic cycloaliphatic or polycycloaliphatic halogenated compounds; and organic aliphatic halogenated compounds such as halogenated paraffins, oligo- or polymers, alkylphosphates or alkylisocyanurates. These comounds are largely known in the art, see such as U.S. Pat. No. 4,579,906 (e.g. col. 3, lines 30-41), U.S. Pat. No. 5,393,812; see also Plastics Additives Handbook, Ed. by H. Zweifel, 5th Ed., Hanser Publ., Munich 2001, pp. 681-698; or tetraphenyl resorcinol diphosphite (FYROFLEX® RDP, Akzo Nobel), chloroalkyl phosphate esters (ANTIBLAZE AB-100, Albright & Wilson; FYROL FR-2, Akzo Nobel), polybrominated diphenyl oxide (DE-60F, Great Lakes Corp.), decabromodiphenyl oxide (DBDPO; SAYTEX 102E), tris[3-bromo-2,2-bis(bromomethyl)propyl]phosphate (PB 370, FMC Corp.), bis(2,3-dibromopropyl ether) of bisphenol A (PE68), brominated epoxy resin, ethylene-bis(tetrabromophthalimide) (SAYTEX BT-93), bis(hexachlorocyclopentadieno)cyclooctane (DECLORANE PLUS), chlorinated paraffins, 1,2-bis(tribromophenoxy)ethane (FF680), tetrabromo-bisphenol A (SAYTEX RB 100 or SAYTEX CP-2000), ethylene bis-(dibromonorbomanedicarboximide) (SAYTEX BN-451), bis-(hexachlorocyclopentadieno)cyclooctane (DECLORANE Plus), tris-(2,3-dibromopropyl)isocyanurate, ethylene-bis-tetrabromophthalimide, 1,2,5,6,9,10-hexabromocyclododecan, ethane-1,2-bis(pentabromophenyl), tetrabromobisphenol A-bis-(allyl ether), dibromocyclohexane, tribromophenol-cyanurate (Dead Sea FR-245), tris (2-chloroethyl)phosphate, tris(2,3-dibromopropyl)phosphate, tris(2,3-dichloropropyl)phosphate, chlorendic acid, tetrachlorophthalic acid, tetrabromophthalic acid, bis(N,N'-hydroxyethyl)tetrachloro-phenylenediamine, a mixture of poly-β-chloroethyltriphosponate, octabromodiphenylether, a derivative of hexachlorocyclopentadiene, ethylene-bis(dibromo-norbornanedicarboximide) (Saytex BN-451), bis-(hexachloorcyclopentadiene)-cyclooctane, polytetrafluoroethylene (Teflon GC) with or without addition of an antimony synergist such as $Sb_2O_3$; tetraphenyl resorcinol diphosphite (FYROFLEX RDP, Akzo Nobel), triphenyl phosphate, ammonium polyphosphate (APP or HOSTFLAM AP750), resorcinol diphosphate ogliomer (RDP), ethylenediamine diphosphate (EDAP), trioctylphosphate, tricresylphosphate, tetrakis(hydroxymethyl)phosphoniumsulfide, diethyl-N,N-bis(2-hydroxyethyl)-aminomethylphosphonate, hydroxyalkylesters of phosphoric acid, phosphazene flame retardants; magnesium hydroxide; zinc oxide, molybdenum trioxide, $Sb_2O_5$, $Sb_2O_3$; melamine phosphate (MELAPUR MP), melamine pyrophosphate, melamine ammonium polyphosphate, melamine ammonium pyrophosphate, melamine cyanurate (MELAPUR MC), melamine borate, melamine polyphosphate (Melapur 200), melamine cyanurate (Melapur MC50); or the reaction product of 2,4-bis[(1-cyclohexyloxy-2,2,6,6-piperidin-4-yl)butylamino]-6-chloro-s-triazine with N,N'-bis(3-aminopropyl) ethylenediamine) [CAS 191680-81-6], 1-(2-hydroxy-2- methylpropoxy)-4-octadecanoyloxy-2,2,6,6-tetramethylpiperidine; or alumina trihydrate, aluminium salt of diethylphosphonic acid (DEPAL); or zinc borate; or oligomeric diisopropyl benzene, silica, silicone, calcium silicate, magnesium silicate, calcium sulfate, magnesium carbonate, or a combination thereof.

The stabilizers and various additives described above may be used alone or in combination and may be added to a polymer to prevent the polymer from thermal degradation due to heating.

Polymer

The polymer is selected from the group consisting of a polyester polyol, a polyether polyol, an acrylic polyol, a polycarbonate polyol, a polybutadiene polyol, a hydrogenated polybutadiene polyol, a functionalized polyether, and polyurethane.

It should be noted that, the compositions of the polyester polyol, the polyether polyol, the acrylic polyol, the polycarbonate polyol, the polybutadiene polyol, the hydrogenated polybutadiene polyol, the functionalized polyether, and/or the polyurethane may also be a foam (flexible, rigid, integral), a microcellular foam, a cast PU, a PU skin, a PU hot melt adhesive, a silylated polyurethane (SPUR), a silyl-terminated polyether, a thermoplastic polyurethane (TPU), a PU elastomer, artificial leather, a PU skin, PU stray coating or reaction injection molding (RIM).

On other hand, the polymer such as the polyether polyol, the polyester polyol, the acrylic polyol, the polycarbonate polyol, the polybutadiene polyol, the hydrogenated polybutadiene polyol, the functionalized polyether, or the polyurethane is not foamed.

For example, commercial products of the acrylic polyol, the polycarbonate polyol, the polybutadiene polyol, the hydrogenated polybutadiene polyol, and the functionalized polyether.

The polyurethane is obtained, for example, by reacting polyether, polyester and polybutadiene which contain terminal hydroxyl groups, i.e. polyols, with aliphatic or aromatic polyisocyanate.

Polyether and polyester having terminal hydroxyl groups are known and are prepared, for example, by polymerizing epoxides such as ethylene oxide, propylene oxide, butylene oxide, tetrahydrofuran, styrene oxide, epichlorohydrin with themselves, for example in the presence of $BF_3$, or by addition reaction of these epoxides, alone or as a mixture or in succession, with starting components containing reactive hydrogen atoms, such as alcohol, ammonia or amine, for example ethylene glycol, propylene 1,3- and 1,2-glycol, trimethylolpropane, 4,4'-dihydroxydiphenylpropane, aniline, ethanolamine or ethylenediamine. Sucrose polyethers are also suitable in accordance with the invention. In many examples, preference is given to those polyethers which predominantly (up to 90% by weight, based on all the OH groups present in the polyether) contain primary OH groups. Furthermore, polyethers modified by vinyl polymers, as are formed, for example, by polymerizing styrene and acrylonitrile in the presence of polyethers, are suitable, as are polybutadienes containing OH groups.

The compounds described above for synthesizing the hydroxy-terminated polyether and polyester are usually having a molecular weight of 40 and are polyhydroxy compounds, especially are compounds with 2 to 8 hydroxyl groups. For instance, the polyether includes at least 2, and usually 2 to 8 hydroxyl groups, and preferably 2 to 4 hydroxyl groups. Moreover, the polyhydroxy compounds described above have a molecular weight of 800 to 10000, and preferably 1000 to 6000. It is known in the art that the polyhydroxy compounds described above are used for preparing the uniform polyurethane and the honeycomb-like polyurethane.

Mixtures of the above compounds containing at least two reactive hydrogen atoms of isocyanate (in particular having a molecular weight of 400-10000) may also be used.

Examples of the polyisocyanates include aliphatic, cycloaliphatic, araliphatic, aromatic, and heterocyclic polyisocyanates, for example, ethylene diisocyanate, 1,4-butyldiisocyanate, 1,6-hexayldiisocyanate, 1,12-dodecane diisocyanate, cyclobutane 1,3-diisocyanate, cyclohexane 1,3-diisocyanate, cyclohexane 1,4-diisocyanate, or a combination of the isomers thereof; 1-isocyanato-3,3,5-trimethyl-5-isocyanatomethylcyclohexane, 2,4-hexahydrotolylene diisocyanate, 2,6-hexahydrotolylene diisocyanate, or a combination of the isomers thereof; hexahydro-1,3-phenylene diisocyanate, hexahydro-1,4-phenylene diisocyanate, perhydro-2,4'-diphenylmethanediisocyanate, perhydro-4,4'-diphenylmethanediisocyanate, 1,3-phenylene diisocyanate, 1,4-phenylene diisocyanate, 2,4-tolylene diisocyanate, 2,6-tolylene diisocyanate, or a combination of the isomers thereof; diphenylmethane-2,4'-diisocyanate, diphenylmethane-4,4'-diisocyanate, naphthylene 1,5-diisocyanate, triphenylmethane 4,4',4"-triisocyanate, polyphenyl-polymethylene polyisocyanates (such as are obtained by aniline-formaldehyde condensation followed by phosgenization), m-isocyanatophenylsulfonyl isocyanates, p-isocyanatophenylsulfonyl isocyanates, perchlorinated aryl polyisocyanates, polyisocyanates containing carbodiimide groups, polyisocyanates containing allophanate groups, polyisocyanates containing isocyanurate groups, polyisocyanates containing urethane groups, polyisocyanates containing acylated urea groups, polyisocyanates containing biuret groups, polyisocyanates containing ester groups, reaction products of the above-described isocyanates with acetals, and polyisocyanates containing polymeric fatty acid groups.

It is also possible to employ the isocyanate group-containing distillation residues as they are or dissolved in one or more of the above-described polyisocyanates, which are obtained in the course of the industrial preparation of isocyanates. Polyisocyanate is preferably the polyisocyanate which may be easily obtained from the industry, such as aromatic polyisocyanates (for example, 2,4-tolylene diisocyanate, 2,6-tolylene diisocyanate, or a combination thereof), polyphenyl-polymethylene polyisocyanates which are obtained by aniline-formaldehyde condensation followed by phosgenization, polyisocyanates (modified polyisocyanates) containing carbodiimide groups, urethane groups, allophanate groups, isocyanurate groups, urea groups, or biuret groups.

The polyurethanes are preferably prepared from the liquid component of raw material (i.e., the material mixed together and reacted with one another by an one shot process).

Composition

The invention provides a composition, which includes the polymers and the stabilizers described above. The preparation method of the composition is as follows. The polymers and the stabilizers are mixed in a glass container to form a mixture at temperature of 60° C. to 65° C. Then, the mixture is stirred at temperature of 60° C. to 65° C. for 30 to 35 minutes. Followed by cooling to the room temperature to obtain the composition.

The step of adding the stabilizers to the polymers may be before or during compounding, extrusion, co-extrusion; before or during polymerization; or before crosslinking. If the stabilizer is added before the polymerization, the stabilizer may be dissolved in one or more of the reactants. The above step of adding the stabilizer to the polymers is preferably by dissolving the stabilizer in the polyester polyol, the polyether polyol, the acrylic polyol, the polycarbonate polyol, the polybutadiene polyol, or the hydrogenated polybutadiene polyol. Also, if needed, the additives may be used in combination.

Based on a content of 100 parts by weight of the polymer, the content of the stabilizer is 0.01 parts by weight to 10 parts by weight, preferably 0.05 parts by weight to 6 parts by weight, and more preferably 0.1 parts by weight to 5 parts by weight.

Furthermore, based on a content of 100 parts by weight of the polymer, the content of the first component of the stabilizer is 0.01 parts by weight to 6 parts by weight and the content of the second component of the stabilizer is 0.03 parts by weight to 9 parts by weight. Preferably, the content of the first component may be 0.05 parts by weight to 5 parts by weight and the content of the second component may be 0.07 parts by weight to 8 parts by weight. More preferably, the content of the first component may be 0.1 parts by weight to 4 parts by weight and the content of the second component may be 0.15 parts by weight to 7 parts by weight.

The composition can be subjected to various processes (such as compression molding, injection molding, extrusion, and rotational molding . . . etc.) to form various products. Specifically, examples of the products described above include:

(1) Adhesive, Coating and Elastomer
(1-1) PU (Polyurethane) Elastomer
(1-1-1) Electrical and electronic industry Bushes, cable connections, components for electrical control and adjustment, electromagnetic switches, hard and elastomeric encapsulants, gear shift cable castings for motor vehicle electrics, insulants, printed circuits, potting, semiconductors, switches, switch gears, medium or high voltage transformers.
(1-1-2) Heavy-duty industry wheels, conveyor belts, sieves or linings.
(1-1-3) Leisure skate board roller.
(1-2) Adhesives
(1-2-1) Automotive bonding of textile onto foam, direct glazing of vehicle windscreens, glazing replacement, fastening of various car components or vacuum lamination of foil to fiberboard
(1-2-2) Building and civil engineering bonding of sandwich insulation panels, flooring, roofs, sealing of car parks, concrete pavements, industrial floors, one component sealant for vertical joints (precast concrete panels, expansion joints) or pourable joint sealants for vertical surfaces (floor-to-wall joints).
(1-2-3) Carpentry furniture assembly and profile lamination of wood to plastic.
(1-2-4) Flexible packaging film-to-film and film-to-foil lamination
(1-2-5) Footwear bonding of shoe soles.
(1-2-6) General industry electronics industry, household goods, loudspeaker acoustic panels, office furniture, metal window frames, air conditioning systems, buses, containers, lorries, metal/sheet metal constructions, railway carriages, sewerage works, silos or ventilation systems.
(1-2-7) Insulated glazing
(1-2-8) Rubbercrumb binding agent for re-milled rubber waste; the composite materials are mainly used as molded tiles, playgrounds (in-situ), running tracks (in-situ).
(1-2-9) Sandwich construction binding of similar substrates together or to other materials such as metals, plastics or rigid foam; or used in a variety of laminated panels, such as panels for buildings, caravans, partition walls, refrigerated trucks, containers or cold storages
(1-3) Polyurethane Hotmelts
(1-3-1) Automotive applications, in particular as instrument clusters, sound insulation, carpeting, seating, decorative trim, exterior applications such as weather stripping, exterior trim, light lens units, or windshield assemblies, recreational vehicle side walls.
(1-3-2) Textile applications, in particular lamination, profile wrapping.
(1-3-3) Furniture industry, in particular for bonding bond solid wood, wood composites, metal hardware, or decorative plastic laminates.
(1-3-4) Construction industry, in particular assembly of door and window frames or corner covering for linoleum flooring.
(2) Thermoplastic polyurethane (TPU)
(2-1) Adhesive Grade
Adhesives for shoe (bond upper to sole), toe caps (powder), furniture, do it yourself or automotive.
(2-2) Extrusion grades
(2-2-1) Cable and wire applications household appliances cables, outdoor electrical cables, industrial cables or wire.
(2-2-2) Hoses and tubes pneumatic transport systems, ventilation systems, pneumatic control units, pneumatic breaks, hydraulic tubes, corrugated pipes, fire hoses, or vacuum cleaner tubes.
(2-2-3) Profile applications round cords, tooth belts, gaskets, bowden cables, stripper blades, or cables.
(2-3) Film and sheet: Typical applications are barrier film, adhesive film, seam tape, or inter layer in security glass.
(2-3-1) Optical applications of aliphatic TPU: Security laminates or security display screens.
(2-3-2) Non-optical applications of aliphatic TPU
Traffic or warning signs, protective films for exterior automotive applications, industrial tapes, industrial boats and balloons, film for food packaging, or aerospace.
(2-3-3) Melt coatings
Belts for food transportation or industrial goods.
(2-4) Injection molding
(2-4-1) General purpose
Ear tags, wheels, horse shoes, plugs, or wrist watch straps
(2-4-2) Hi-performance/special compounds
Transparent soles for sport shoes, frames for ski goggles, technical parts, or screens (mining).
(2-4-3) Automotive applications
Gear shift knobs, bearing sockets, cable plugs, bushings, casings, or friction bearings.
(2-4-4) Seal applications
Hydraulic seals, stripper rings, gaskets, pneumatic seals, or membranes
(3) Automotive applications
Bumpers, dashboards, battery, rear and front linings, moldings parts under the hood, hat shelf, trunk linings, interior linings, air bag covers, electronic moldings for fittings (lights), panes for dashboards, headlamp glass, instrument panel, exterior linings, upholstery, automotive lights, head lights, parking lights, rear lights, stop lights, interior and exterior trims; door panels; gas tank; glazing front side; rear windows; seat backing, exterior panels, wire insulation, profile extrusion for sealing, cladding, pillar covers, chassis parts, exhaust systems, fuel filter/filler, fuel pumps, fuel tank, body side moldings, convertible tops, exterior mirrors, exterior trim, fasteners/fixings, front end module, glass, hinges, lock systems, luggage/roof racks, pressed/stamped parts, seals, side impact protection, sound deadener/insulator or sunroof.

(3-1) Flexible Foam, in particular arm rest, head restraints, acoustic foam carpet, or seats.

(3-2) Semi-rigid foam, in particular roof liners, hat racks, door panels, arm rest, instrument panel, head-impact, or side-impact.

(3-3) Rigid foam, in particular foam filling of cavities.

(3-4) Flexible integral foam, in particular steering wheel, air filter, gearshift knob, spoiler, cable sheeting, or head restraints.

(3-5) RIM, in particular bumpers, sun roof, front and rear skirts, or door sill scuff plates.

(3-6) TPU, in particular front and rear skirts, doorsill scuff plates, cable sheeting, gearshift knob, instrument panel.

(3-7) Cast PU systems, in particular spring aids, spring isolation, seat damping, top mounts, roll restrictors, emergency wheel, body mounts, or stops in door systems.

(4) Footwear

Shoes/shoe-soles (insoles, spats, adhesives, structural adhesives)

(5) Furniture (6) Support devices articles for the leisure time such as sports and fitness devices, gymnastics mats, ski-boots, inline-skates, skis, big foot, or athletic surfaces (e.g. tennis grounds)

(7) Others

Composite panels, insulation board and block, technical insulation, pipe insulation, food boxes (fruit, vegetables, meat, fish), synthetic paper, labels for bottles, couches, human artificial joints, printing plates (flexographic), printed circuit boards, display technologies, screw tops, tops and stoppers for bottles, or cans. For example, PU elastomers, PU skin, PU spray coating, TPU, PU artificial leather, silylated polyurethane (SPUR), PU hot melt adhesives, Cast PU, PU foam (flexible, rigid, integral), PU microcellular, or reaction injection molding (RIM).

The synthetic method of 4-((8-((bis((1,2,2,6,6-pentamethylpiperidin-4-yl)phosphanyl)oxy)-4-methyl-1-(1,2,2,6,6-pentamethylpiperidin-4-yl)-1,3,6-trioxa-2-phosphanonan-2-yl)oxy)-1,2,2,6,6-pentamethylpiperidine (product name: Chinox MP, chemical A-3 in Table 1)

In a flask, place into 100 parts by weight of oxybispropylenebis(1,5,9,13,17,21-hexamethyl-7,15,23,23-tetraphenoxy-3,6,8,11,14,16,19,22-octaoxa-7,15,23-triphosphatricos-1-yl)(phenyl)phosphine (product name: Chinox TP-20, CAS No. 80584-86-7, manufactured by DOUBLE BOND CHEMICAL IND., CO., LTD.), 77.2 parts by weight of 1,2,2,6,6-pentamethyl-4-piperidinol, and 0.2 parts by weight of sodium methoxide. Heat and stir for three hours at a temperature of 145° C. and under a nitrogen atmosphere. After stirring for 3 hours, 1,2,2,6,6-pentamethyl-4-piperidinol in the reaction mixture obtained is less than 1 wt % (measured by gas chromatography). Subsequently, the nitrogen atmosphere in the flask is replaced with a vacuum, and 65 parts by weight of a by-product phenol is distilled out under the vacuum (degree of vacuum is 3 mm-Hg, and distillation time is 6 hours). Next, the temperature is reduced to 120° C. Then, the distilled mixture is filtered by a diatomite, so as to obtain a 103 parts by weight of the Chinox MP.

EXAMPLES

Example 1

In a glass vessel, 100 parts by weight of polyether polyol (Bayer ARCOL POLYOL 5603) and 0.3 parts by weight of a stabilizer (e.g., the component A-1 in Table 1) are mixed at 65° C. to form a mixture. Then, the mixture is stirred at 65° C. for 30 minutes. Followed by cooling to the room temperature.

Examples 2 to 5

The composition of example 2 to example 5 are prepared using the same methods as example 1, with the difference being: the type of the ingredients and the usage amount thereof are changed (as shown in Table 2), wherein the compounds corresponding to the labels (A-1, A-2, A-3, B-1, B-2, C-1, and D-1) of Table 2 are as shown in Table 1.

Comparative Example 1

The composition of comparative example 1 is a blank test, that is, without adding any stabilizer. Also, the method for preparing the composition of comparative example 2 is stirring 100 parts by weight (30 g) of polyether polyol (Bayer ARCOL POLYOL 5603) in a glass vessel at 65° C. for 30 minutes. Followed by cooling to the room temperature.

Comparative Example 2

The composition of comparative example 2 is prepared using the same methods as example 1, with the difference being: the type of the ingredients and the usage amount thereof are changed (as shown in Table 2), wherein the compounds corresponding to the labels (A-1, A-2, A-3, B-1, B-2, C-1, and D-1) of Table 2 are as shown in Table 1. It should be noted that, the stabilizer used in comparative example 2 is a standard commonly used to evaluate the stabilizer.

Measurement of Differential Scanning Calorimetry

Oxidation resistance of the polymer (i.e., the degree of thermal degradation resistance) is measured according to differential scanning calorimetry. In an embodiment, the model of a differential scanning calorimeter is NETZSCH DSC 200 F3.

Measurement of Oxidative Induction Temperature (OIT) (a)

Take 15 mg of the samples (which are the compositions) obtained in examples or comparative examples and place them into the differential scanning calorimeter. Next, the above-described samples obtained in examples or comparative examples are heated under oxygen atmosphere, wherein a heating temperature ranges from 50° C. to 280° C., and a heating rate is 5° C./min. Then, an exothermic peak is observed from a thermal analysis curve obtained by the differential scanning calorimetry, wherein a temperature corresponding to the starting point of the exothermic peak is an oxidative induction temperature (OIT) (a).

The higher the OIT (a), the higher the oxidation resistance of the polymer (i.e., the degree of the thermal degradation resistance of the polymer is higher), which means that the degree of the thermal degradation resistance of the polymer may be effectively enhanced by the stabilizer. OIT (a) of the polymers of example 1 and comparative example 1 to comparative example 6 are shown in Table 2.

Measurement of Oxidative Induction Temperature (OIT) (b)

Take 15 mg of the samples obtained in examples or comparative examples and place them into the differential scanning calorimeter. Next, the above-described samples obtained in examples or comparative examples are heated first under nitrogen atmosphere, wherein the heating temperature ranges from 50° C. to 180° C., and the heating rate is 20° C./min. Next, the nitrogen atmosphere is converted to an oxygen atmosphere at 180° C. (the flow rate of oxygen and the flow rate of nitrogen are the same). Then, observe from the thermal analysis curve at the constant temperature of 180° C. After converting to the oxygen atmosphere, as compared to the reference ($Al_2O_3$), the time required for the sample to start the exothermic reaction is observed, wherein the time required for the exothermic reaction is an oxidative induction temperature (OIT) (b).

The higher the OIT (b), the higher the thermal stability of the polymer at high temperature (i.e., the degree of the thermal degradation resistance of the polymer is higher), which means that the degree of the thermal degradation resistance of the polymer may be effectively enhanced by the stabilizer. OIT (b) of the polymers of example 1 and comparative example 1 to comparative example 6 are shown in Table 2.

Evaluation Results

Table 2 shows the OIT (a) and the OIT (b) of the polymers of example 1 to example 5 and comparative example 1 to comparative example 2.

The composition of comparative example 1 does not contain the stabilizer, and the OIT (a) and the OIT (b) are lower. In contrast, the composition of example 1 to example 5 and comparative example 2 all contain the stabilizer, and the OIT (a) and the OIT (b) are all higher. This result shows that the addition of the stabilizer into the polymer may effectively enhance the degree of the thermal degradation resistance of the polymer. Also, cost of the stabilizer of example 4 is lower, which facilitates the applications.

The stabilizer used in comparative example 2 is a standard commonly used to evaluate the stabilizer. Comparing to comparative example 2, the OIT (a) of example 1, example 2, example 3, and example 5 are low, and the OIT (b) thereof are high. This result shows that the stabilizer containing the first component or phosphites, or phosphonites C may enhance the degree of the thermal degradation resistance of the polymer.

In addition, according to those described in example 1 to example 3, when the stabilizer is composed of the first component, the degree of the thermal degradation resistance of the polymer may be effectively enhanced. Also, when the stabilizer is the compound A-3, the thermal degradation resistance is much better.

TABLE 1

| | |
|---|---|
| A-1 | oxybispropylenebis ((1,5,9,13,17,21-hexamethyl-7,15,23,23-tetraphenoxy-3,6,8,11,14,16,19,22-octaoxa-7,15,23-triphosphatricos-1-yl)(phenyl)phosphine) (product name: Chinox TP-20, CAS No. 80584-86-7, manufactured by DOUBLE BOND CHEMICAL IND., CO., LTD.) |
| A-2 | 1-(2-bis(2,4-di-tert-butylphenoxy)phosphanyloxypropoxy)propan-2-yl-bis(2,4-di-tert-butylphenyl) phosphate (product name: Chinox TP-80, manufactured by DOUBLE BOND CHEMICAL IND., CO., LTD.) |
| A-3 | 4-((8-((bis((1,2,2,6,6-pentamethylpiperidin-4-yl)phosphanypoxy)-4-methyl-1-(1,2,2,6,6-pentamethylpiperidin-4-yl)-1,3,6-trioxa-2-phosphanonan-2-yl)oxy)-1,2,2,6,6-pentamethylpiperidine (product name: Chinox MP, manufactured by DOUBLE BOND CHEMICAL IND., CO., LTD.) |
| B-1 | a mixture of heptyl 3-(3,5-di-tert-butyl-4-hydroxyphenyl)propionate, octyl 3-(3,5-di-tert-butyl-4-hydroxyphenyl)propionate, and nonyl 3-(3,5-di-tert-butyl-4-hydroxyphenyl)propionate (product name: Chinox 35, manufactured by Double Bond Chem. Ind., Co., Ltd.) |
| B-2 | heptyl 3-(3,5-di-tert-butyl-4-hydroxyphenyl)propionate (product name: Chinox P1014, manufactured by Double Bond Chem. Ind., Co., Ltd.) |
| C | tris-dodecyl-phosphite (product name: Chinox 312, manufactured by Double Bond Chem. Ind., Co., Ltd.) |
| D | products of N-phenyl-Benzenamine react with 2,4,4-trimethylpentene (product name: IRGANOX 5057, CAS No. 68411-46-1, an aromatic amine antioxidant, manufactured by Ciba, Co., Ltd.) |
| Polymer | polyether polyol (Bayer ARCOL POLYOL 5603) |

TABLE 2

| | | | Example | | | | | Comparative example | |
|---|---|---|---|---|---|---|---|---|---|
| | | | 1 | 2 | 3 | 4 | 5 | 1 | 2 |
| Stabilizer (parts by weight) | The first component A (parts by weight) | A-1 | 0.3 | — | — | 0.1 | — | — | — |
| | | A-2 | — | 0.3 | — | — | — | — | — |
| | | A-3 | — | — | 0.3 | — | — | — | — |
| | The second component B (parts by weight) | B-1 | — | — | — | 0.1 | — | — | 0.2 |
| | | B-2 | — | — | — | 0.1 | — | — | — |
| | phosphites, or phosphonites C (parts by weight) | | — | — | — | — | 0.3 | — | — |
| | D (parts by weight) | | — | — | — | — | — | — | 0.1 |

TABLE 2-continued

|  | Example | | | | | Comparative example | |
|---|---|---|---|---|---|---|---|
|  | 1 | 2 | 3 | 4 | 5 | 1 | 2 |
| polyether polyol (parts by weight) | 100 | 100 | 100 | 100 | 100 | 100 | 100 |
| OIT (a) (° C.) | 202.7 | 210.6 | 219.9 | 198.3 | 199.7 | 197.8 | 203.2 |
| OIT (b) (minute) | 20.7 | 38.7 | 83.9 | 50.9 | 41.2 | 3.2 | 15.3 |

According to the above, in the invention, by including the first component of a poly(dipropylene glycol) phosphite-based compound, the second component of alkyl 3-(3,5-di-tert-butyl-4-hydroxyphenyl)propionate, or a combination thereof in the stabilizer, the issue of poor degree of thermal degradation resistance of the known polymer may be solved.

It will be apparent to those skilled in the art that various modifications and variations may be made to the structure of the disclosed embodiments without departing from the scope or spirit of the invention. In view of the foregoing, it is intended that the disclosure cover modifications and variations of this specification provided they fall within the scope of the following claims and their equivalents.

What is claimed is:

1. A stabilizer, comprising:
a first component, represented by formula (1),

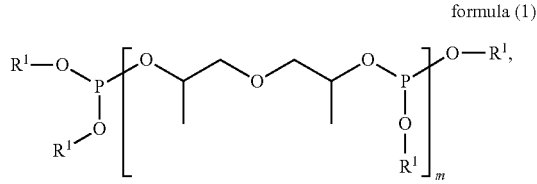

formula (1)

wherein $R^1$ is selected from the group consisting of a $C_6$-$C_{15}$ aryl group, a $C_6$-$C_{15}$ aryl group having a substituent, and a $C_6$-$C_{15}$ heterocyclic group having a substituent, and m is selected from integers of 1 to 8, wherein the substituent comprises a straight chain or a branch chain C1-C18 alkyl group or a C6-C15 aryl group, and a heteroatom comprised in the C6-C15 heterocyclic group having a substituent is selected from the group consisting of a nitrogen atom, an oxygen atom, and a sulfur atom; and a second component, represented by formula (2),

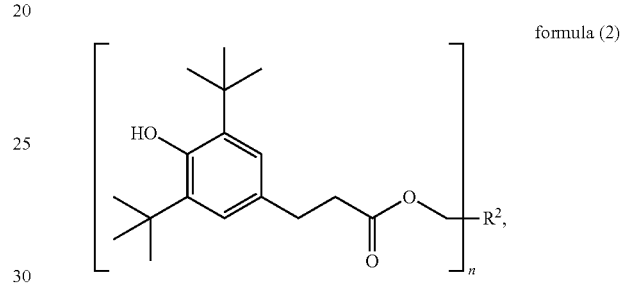

formula (2)

wherein n is 1 or 4, when n is 1, $R^2$ is a $C_1$-$C_{18}$ alkyl group, and when n is 4, $R^2$ is 2,2-dimethylprop-1,3,1',1"-tetrayl, and wherein based on 100 wt % of the first component and the second component, a content of the first component is 10 wt % to 60 wt %, a content of heptyl 3-(3,5-di-tert-butyl-4-hydroxyphenyl)propionate, octyl 3-(3,5-di-tert-butyl-4-hydroxyphenyl)propionate, and nonyl 3-(3,5-di-tert-butyl-4-hydroxyphenyl)propionate of the second component is 20 wt % to 80 wt %, and a content of methyl 3-(3,5-di-tert-butyl-4-hydroxyphenyl)propionate of the second component is 10 wt % to 70 wt %.

2. The stabilizer of claim 1, wherein the first component is selected from the group consisting of a compound represented by formula (1-1), a compound represented by formula (1-2), and a compound represented by formula (1-3),

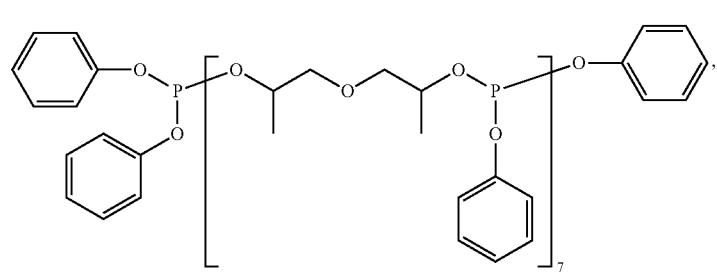

formula (1-1)

formula (1-2)

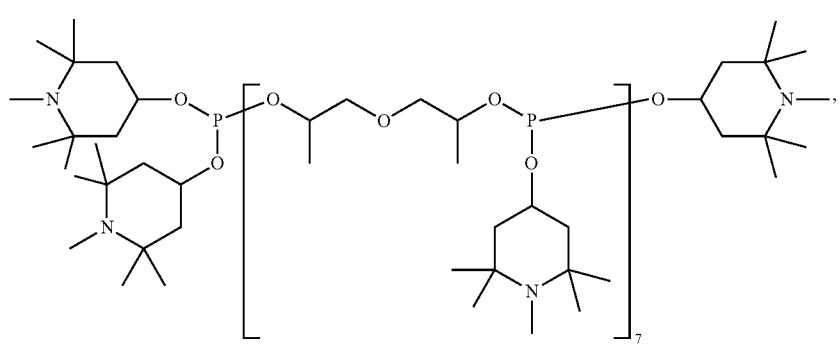

formula (1-3)

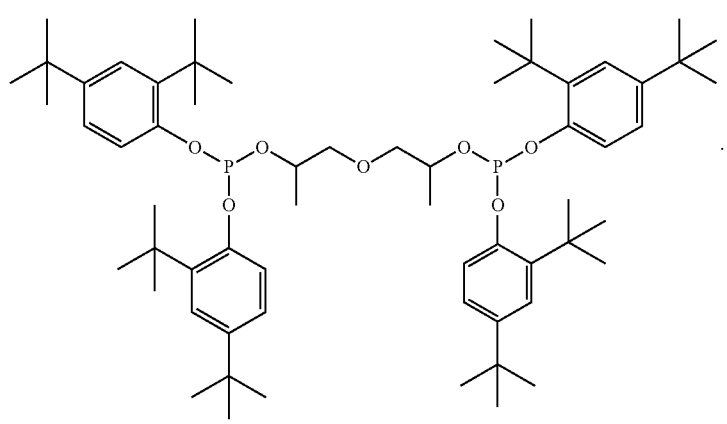

3. A composition, comprising:
a polymer; and
the stabilizer of claim 1, wherein based on 100 parts by weight of the polymer, a content of the stabilizer is 0.01 parts by weight to 10 parts by weight.

4. The composition of claim 3, wherein the polymer is selected from the group consisting of a polyester polyol, a polyether polyol, an acrylic polyol, a polycarbonate polyol, a polybutadiene polyol, a hydrogenated polybutadiene polyol, a functionalized polyether, and polyurethane.

* * * * *